United States Patent [19]

Eggleston et al.

[11] Patent Number: 5,628,798
[45] Date of Patent: May 13, 1997

[54] ADJUSTABLE AND REMOVABLE INTRAOCULAR LENS IMPLANT

[75] Inventors: Harry C. Eggleston, 499 Rosslare Dr., St. Charles, Mo. 63304; Thom Day, Cole County, Mo.

[73] Assignee: Harry C. Eggleston, St. Charles, Mo.; a part interest

[21] Appl. No.: 617,183

[22] Filed: Mar. 18, 1996

[51] Int. Cl.⁶ ............................................. A61F 2/16
[52] U.S. Cl. ................................................. 623/6
[58] Field of Search ................. 623/6, 5; 315/160 R, 315/161

[56] References Cited

U.S. PATENT DOCUMENTS

| | | |
|---|---|---|
| 3,458,870 | 8/1969 | Store, Jr. ............ 623/6 |
| 4,373,218 | 2/1983 | Schachar . |
| 4,564,267 | 1/1986 | Nishimoto . |
| 4,575,373 | 3/1986 | Johnson . |
| 4,601,545 | 7/1986 | Kern . |
| 4,731,078 | 3/1988 | Stoy et al. . |
| 4,816,031 | 3/1989 | Pfoff . |
| 4,863,468 | 9/1989 | Feinbloom et al. ........ 623/6 |
| 4,932,966 | 6/1990 | Christie et al. . |
| 4,932,971 | 6/1990 | Kelman . |
| 5,030,231 | 7/1991 | Portney . |
| 5,108,429 | 4/1992 | Wiley . |
| 5,171,266 | 12/1992 | Wiley et al. . |
| 5,203,788 | 4/1993 | Wiley . |
| 5,222,981 | 6/1993 | Werblin . |
| 5,326,347 | 7/1994 | Cumming . |

*Primary Examiner*—Mary Beth Jones
*Attorney, Agent, or Firm*—Paul M. Denk

[57] ABSTRACT

An adjustable ocular IOL/insert to be implanted during refractive cataract surgery and clear (human) crystalline lens refractive surgery and adjusted post-surgically. The implant comprises relatively soft but compressible and resilient base annulus designed to fit in the lens capsule and keep the lens capsule open. Alternatively the annulus may be placed in the anterior or posterior chamber. There is a second concentric annulus removably seated in the outer annulus. The second annulus has a threaded inner surface. A rotatable annular lens mount, bearing an appropriate lens, is threadedly engaged in the second annulus. The lens mount is rotated to move the lens forward or backward so to adjust and fine tune the refractive power and focusing for hyperopia, myopia and astigmatism. The intraocular implant has a power range of approximately +3←0→–3 diopters. The second annulus can be removed from the base annulus and lifted out of the eye so that the rotatable lens assembly can be changed, adjusted, modified or entirely removed with new assembly placed for the patient's changing visual needs and lifestyle with less stress on the base annulus and on the rotatable lens assembly.

5 Claims, 5 Drawing Sheets

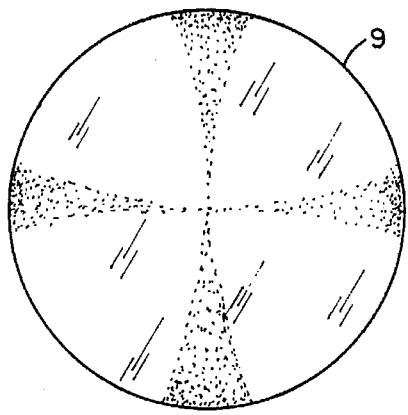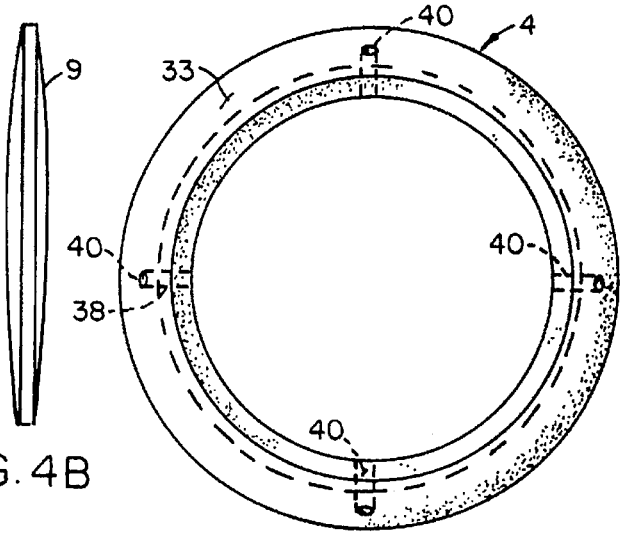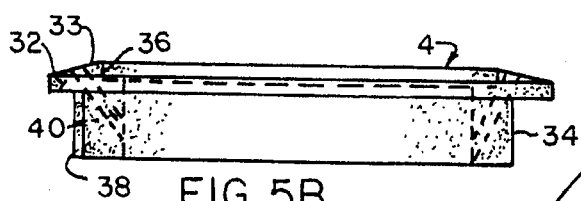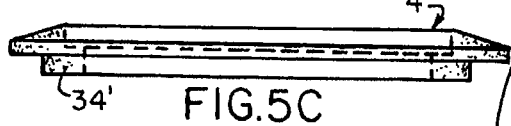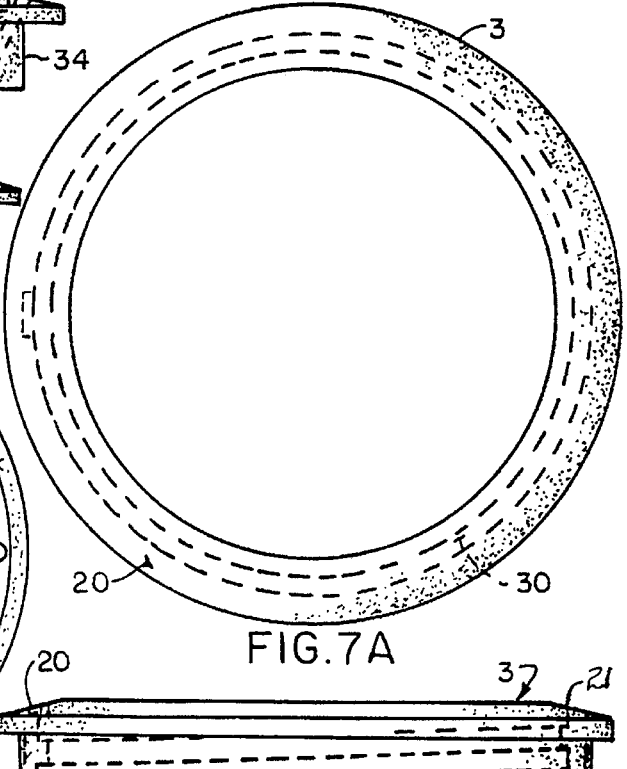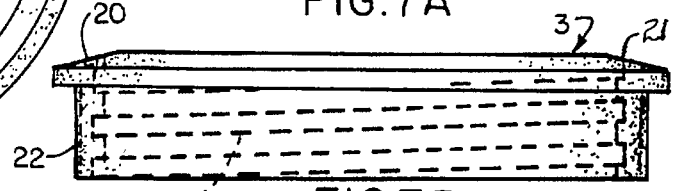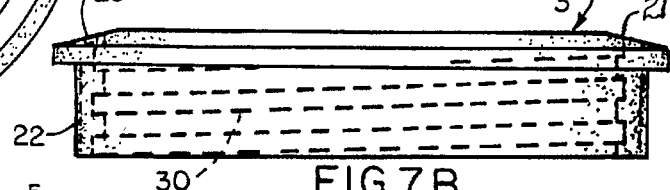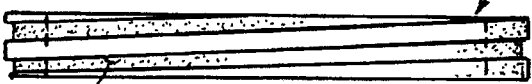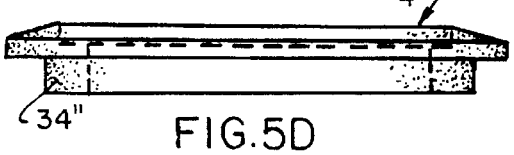

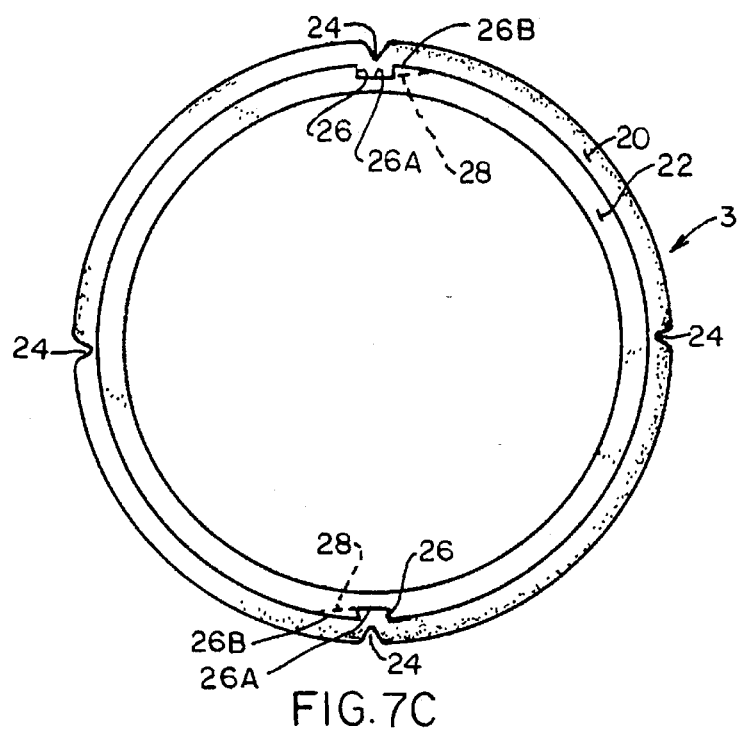
FIG.7C
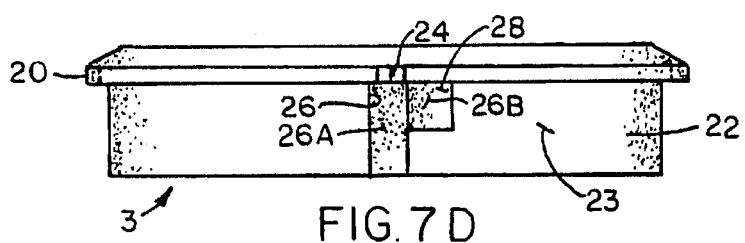
FIG.7D
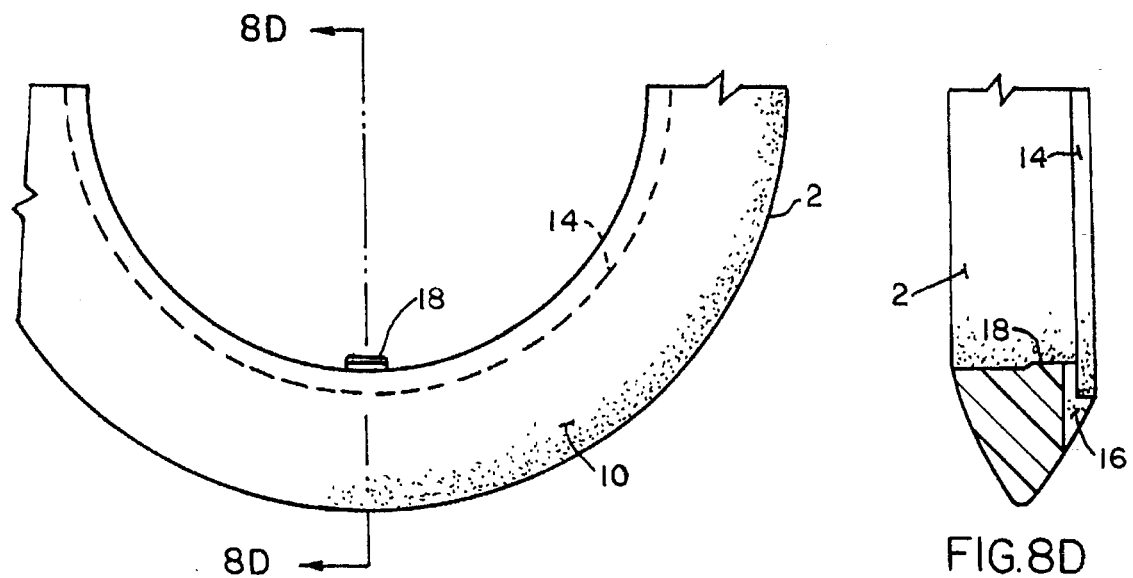
FIG.8C
FIG.8D

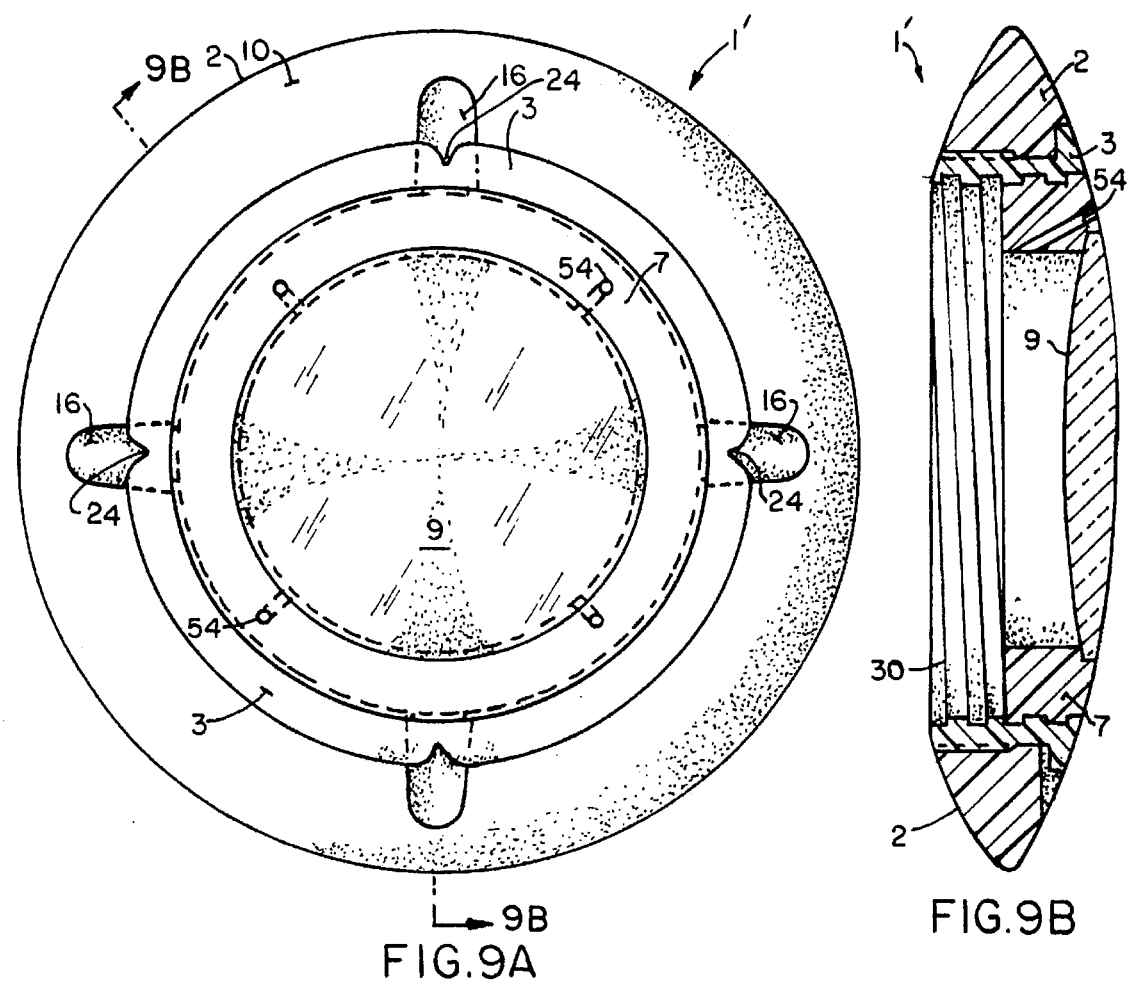
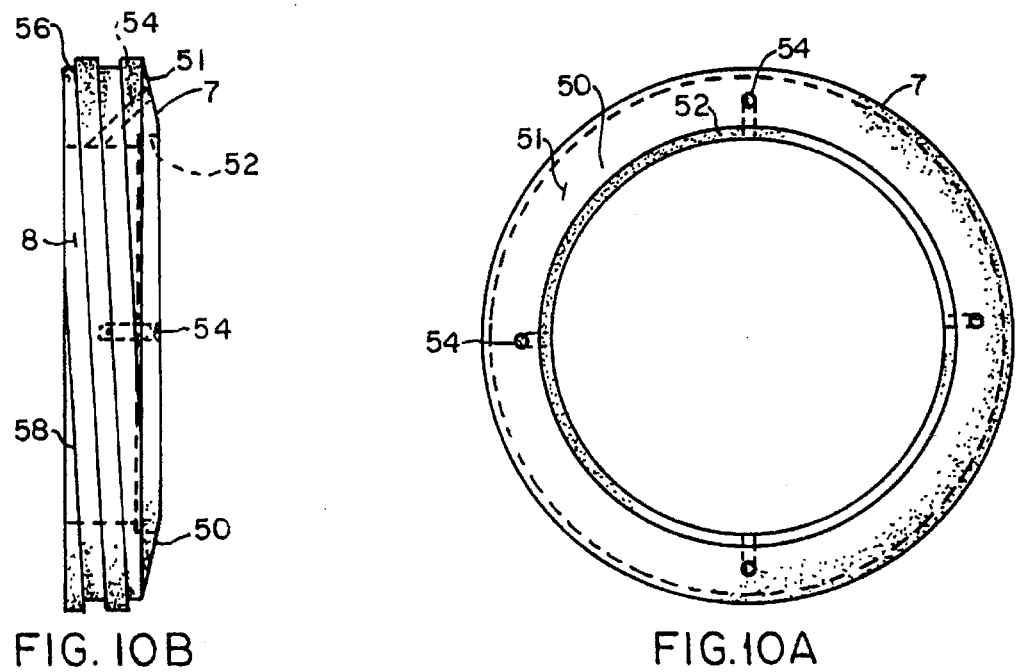
FIG.9A FIG.9B
FIG.10B FIG.10A

ADJUSTABLE AND REMOVABLE INTRAOCULAR LENS IMPLANT

BACKGROUND OF THE INVENTION

This invention relates generally to ocular implants and more specifically to a modular ocular implant with an adjustable and replaceable lens.

A cataract is a condition where a normally clear lens of the eye becomes progressively opaque. The opacification generally occurs over a period of time and the amount of light which passes through the lens decreases thereby decreasing vision. It is necessary, therefore, to surgically remove and replace the clouded lens. Often, there is a coexistent refractive defect such as myopia (short sightedness), hyperopia and astigmatism.

Generally the lens is removed for cataract or clear lens refractive purposes for high myopia and hyperopia, and is replaced at the time of surgery with an intraocular lens formed from a biocompatible material such as PMMA (polymethyl methacrylate) or the like. The surgeon makes an incision in the sclera and cornea to allow the removal of the semi-opaque lens and/or clear lensectomy and insertion of the implant. The typical prior art lens implant is either of plano-convex design or double convex design, with each curved surface defining a spherical section. A large number of patients will have significant post-surgical astigmatism and spherical error and will need a spherical/astigmatic adjustment in their glasses. The surgery can induce astigmatism which can fluctuate greatly over time after surgery, as can the lens capsule (bag), zonules, etc.

One problem associated with intraocular lens implants is that it is necessary to decide, preoperatively, on the power of the lens. This can be done by performing various standard (ultrasound) procedures such as a preoperative refraction and keratometric determinations and then making an estimate of the proper power of lens to determine proper refraction of the eye. Although the ophthalmologist uses the best techniques available, it is very difficult to accurately predict, preoperatively, the optimal power for the lens implant because of multiple variables of axial length, anterior chamber depth, corneal curvature and size, growth of the eye (pediatric cases), irregular post scleral surfaces (usually seen in the macular area) such as myopic staphylomas, mismeasurement and mislabeling of the IOL power and other human errors. Therefore, most patients are required to use glasses for precise focusing even after the replacement of the semi-opaque lens. Further, since the exact amount and axis of astigmatism cannot be accurately determined until several weeks after surgery, the patient may require glasses for best vision and the lens prescription may have to be changed more than once as the eye heals over time, because of different visual needs.

Several intraocular lenses which allow post-surgical correction are known. U.S. Pat. No. 4,575,373 discloses a laser adjustable intraocular lens. U.S. Pat. No. 4,816,031 provides a lens implant with a second soft and pliable lens position over it and electromechanical circuitry for regulating the distance between the two lenses.

U.S. Pat. No. 4,601,545 discloses a variable power lens having optically active molecular material, such as liquid crystals than can be configured using electrical voltages. U.S. Pat. No. 4,564,267 discloses a variable focal length lens which can be electrically controlled by applying an electric field to a compound lens with one lens formed of electrooptic crystals.

U.S. Pat. No. 4,373,218 discloses a variable power intraocular lens including a fluid expandable sac for containing a liquid crystal material that responds to electric charge to change the index of refraction of the lens.

U.S. Pat. No. 4,932,966 discloses a intraocular lens apparatus having a flexible lens member and with a relatively rigid portion with fluid-filled chambers therebetween. The shape or position of the lens portion is adjusted by changing fluid pressure in the fluid-filled chambers.

U.S. Pat. No. 4,932,971 provides a clip-on optic assembly for clipping in situ onto a previously implanted intraocular lens to change its optical characteristics without removal from the eye.

U.S. Pat. No. 5,108,429 provides an adjustable focus lens with a plurality of micromotor devices spaced around the periphery of the lens body, the devices being responsive to an external control signal for selectively changing the position of a lens body. U.S. Pat. No. 5,203,788 also provides an adjustable lens apparatus having a lens body with a relatively rigid outer ring with micromotors between the lens body and the outer ring that are responsive to outside actuation.

U.S. Pat. No. 5,171,266 discloses an intraocular lens having a flexible lens body center portion surrounded by an outer ring which is sensitive to an external force such as a magnetic force. The shape of the outer body can be changed by magnetic force to elongate the lens body. U.S. Pat. No. 5,326,347 also discloses an intraocular implant that is responsive to the post-surgical application of force, such as the movement of the implantee's head and magnetic force to change the focus.

Although the foregoing devices may solve the problem of adjustment of the lens post-surgically, there have other inherent drawbacks. Some of the adjustable lens are complicated in design employing power sources, micromotors, microfluid pumps and electric or electrochemical circuitry. Such complex devices can be expensive to manufacture and relatively bulky or heavy in use. Some adjustable lenses require the use of external adjustment technology such as electric current, magnets or other forces.

SUMMARY OF THE INVENTION

It is, therefore, among the principal objects of the present invention to provide an adjustable ocular implant, even one that can be adjusted in situ.

It is another object of the present invention to provide an adjustable and upgradeable ocular lens implant to allow for improvements in optical resolution, wave length management and new technologies that can be adjusted post-surgically to improve focus.

It is yet another object of the present invention to provide an adjustable ocular implant that is relatively simple and elegant in design.

Still another object of the present invention is to provide an adjustable ocular implant that is lightweight and easily implanted during cataract surgery.

Yet another object of the present invention is to provide an adjustable ocular implant that allows for the simple replacement of a corrective lens.

Another object of the present invention is to provide an adjustable ocular implant that does not require the use of complex techniques or peripheral devices to effect adjustment of the implant after surgery.

Yet another object of the is to provide an adjustable ocular implant that will adjust and fine tune the refractive power and focusing for hyperopia, myopia and astigmatism.

In accordance with the invention, an adjustable ocular implant is provided that can be implanted during cataract surgery and/or clear lensectomy and easily adjusted post-surgically. The implant comprises relatively soft but compressible and resilient outer or base annulus designed to fit in the lens capsule and keep the lens capsule open. Alternatively the annulus may be placed in the anterior or posterior chamber. There is a second concentric annulus removably seated in the outer annulus. The second annulus can have a threaded inner surface or be lined with a threaded insert. A rotatable annular lens mount, bearing an appropriate lens, is threadedly engaged in the second annulus. The lens mount can be rotated with an appropriate tool to move the lens forward or backward so to adjust and fine tune the refractive power and focusing for hyperopia, myopia and astigmatism. The intraocular implant has a correction range for spherical correction of approximately +3←-0-→-3 diopters with probable steps of 0.50 diopters and for astigmatic correction of +1 to +4 with an overlay lens. The second annulus can be removed from the base annulus and lifted out of the eye so that the rotatable lens assembly can be changed with less stress on the base annulus lens zonule capsule on the rotatable lens assembly.

BRIEF DESCRIPTION OF THE DRAWINGS

FIG. 4A is a front plan of the clear lens of the adjustable ocular implant of the present invention;

FIG. 4B is a side elevational view thereof;

FIG. 5A is a front plan of one preferred embodiment of the lens mount of the adjustable ocular implant of the present invention;

FIG. 5B is a slide elevational view thereof;

FIG. 5C is a side elevational view of another embodiment of the lens mount of the adjustable ocular implant of the present invention;

FIG. 5D is a side elevational view of another embodiment of the lens mount of the adjustable ocular implant of the present invention;

FIG. 6A is a top plan of a threaded insert of the adjustable ocular implant of the present invention;

FIG. 6B is a side elevational view thereof;

FIG. 7A is a top plan of the second annulus of the adjustable ocular implant of the present invention;

FIG. 7B is a side elevational view thereof;

FIG. 7C is a bottom plan thereof;

FIG. 7D another side elevation view thereof;

FIG. 8C is a partial section of the base annulus of FIG. 8A;

FIG. 8D is a cross-sectional view taken along line 8D—8D of FIG. 8C;

FIG. 9A is a another front plan of the adjustable ocular implant of the present invention;

FIG. 9B is another cross-sectional view of the adjustable ocular implant of the present invention taken along line 9B—9B of FIG. 9A;

FIG. 10 A is a front plan of one preferred embodiment of the lens mount of the adjustable ocular implant of the present invention; and FIG. 10B is a side elevational view thereof.

Corresponding reference figures indicate corresponding structures throughout the various drawings.

DESCRIPTION OF THE PREFERRED EMBODIMENT

Figure 1:
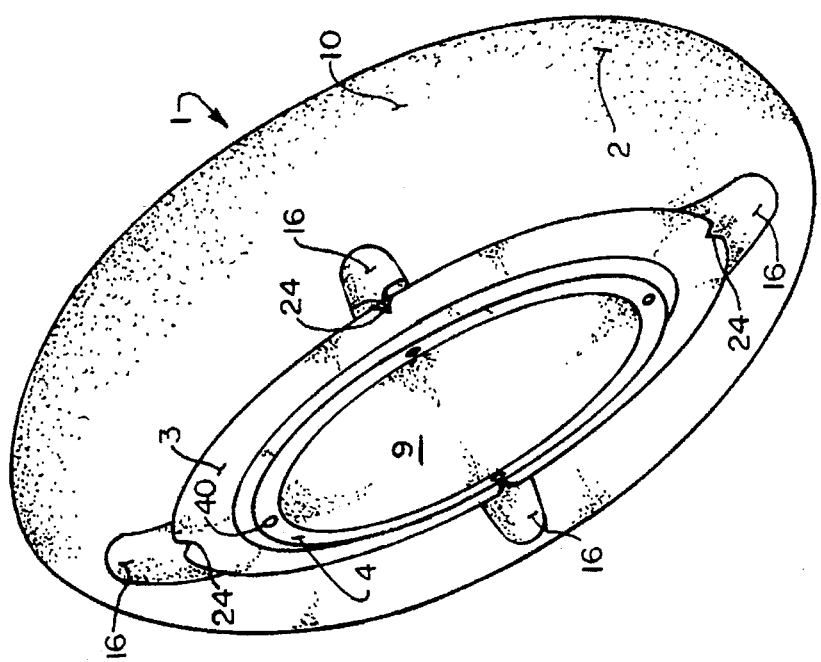
FIG. 1 is an isometric view of the adjustable ocular implant of the present invention.
Figure 2:
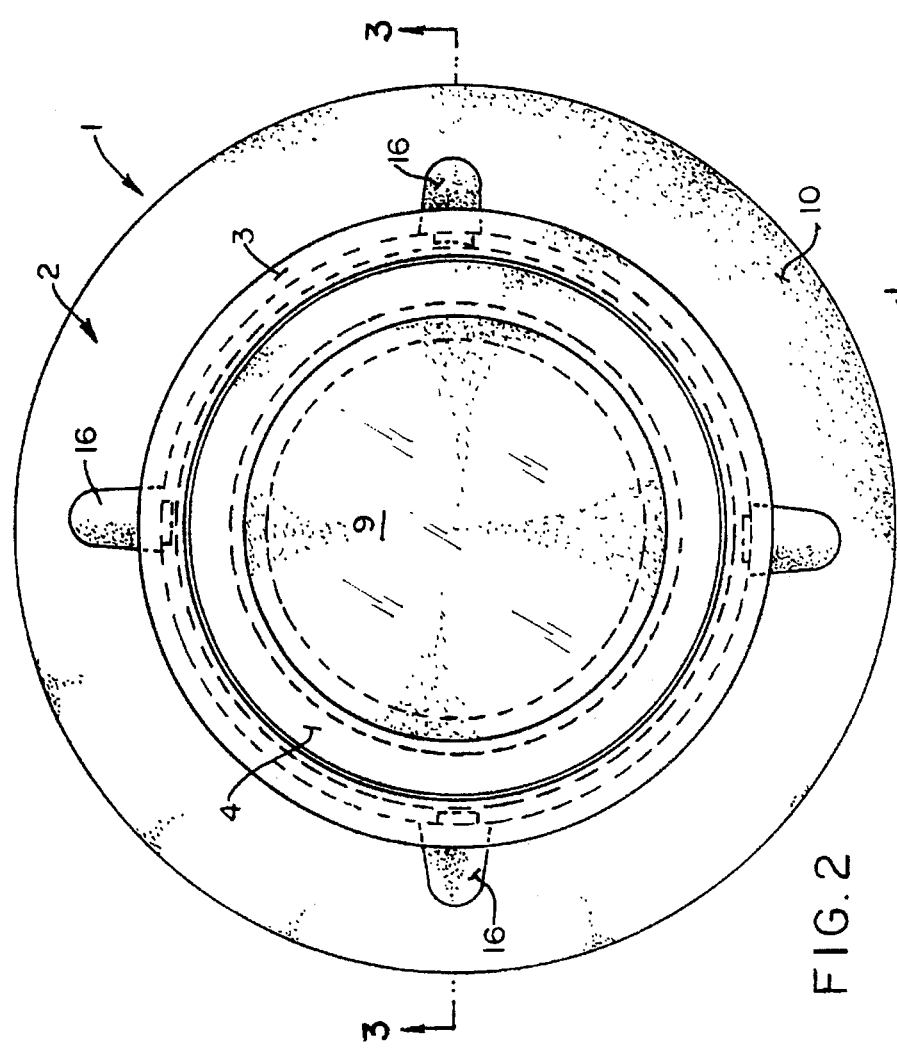
FIG. 2 is a front plan thereof.

The adjustable intraocular insert of the present invention is indicated generally by reference numeral 1 in the drawings. Insert 1 has several principal components including an outer or base annulus 2 and a concentric second annulus 3. An adjustable lens mount assembly, indicated generally by reference numeral 4 in FIGS. 5A and 5B, is rotatably mounted in second annulus 3. In the preferred embodiment of FIGS. 1–3, the lens mount assembly 4 comprises two pieces, employing an externally threaded ring 5. Another embodiment of the adjustable intraocular insert, indicated generally be reference numeral 1' in FIGS. 9A and 9B, employs a one-piece lens holder 7 (FIGS. 10A and 10B) which includes an externally threaded annular skirt 8. In any event, the lens holder seats a refractive lens 9. The various components of the adjustable intraocular insert will now be described in greater detail.

The base annulus 2, shown in greater detail in FIGS. 8A–8D, is sized and configured to fit into the capsular bag of the human eye after a cataract has been removed. Alternatively, annulus 2 can be configured to be placed in the ciliary sulcus or anterior chamber. Annulus 2 has a compressible, resilient annular body 10 made of a biologically compatible, relatively inert material such as PMMA, silicone or the like. As shown, body 10 defines a central, substantially circular opening 12. There is a rabbet 14 formed around the peripheral edge of opening 12 to seat the second annulus 3, as will be described below. Also formed in the face of body 19 are a plurality of indentions or notches 16. In the illustrated embodiment, four notches 16 are formed in the face of body 10 and spaced equidistant around the face of the body. The notches 16 are in communication with rabbet 14 and are formed to allow an ophthalmologist or technician access to the second annulus as will be explained below. As can best be seen in FIGS. 8C and 8D, there is a raised detent 18 formed on the inner surface of the annulus. There is a second detent 18 directly across from the first. Detents 18 are designed to engage complementary slots formed in the second annulus 3 in a bayonet-type lock, as will now be explained.

The second annulus 3 is best shown in FIGS. 7A and 7B. Annulus 3 has outer ring 20 with a beveled leading edge 21 and a concentric annular skirt 22. Skin 22 has a generally smooth outer surface 23. It will be appreciated that outer ring 20 is dimensioned to seat in rabbet 14 of the base annulus when the intraocular insert is fully assembled. Outer ring 20 has a plurality of V-shaped grooves 24 formed therein. The embodiment shown includes four grooves 24 placed equidistant around the ring which are designed to accept a tool for the application of torque so as to rotate annulus 3 for the introduction or removal of annulus 3 from base annulus 2. It will be appreciated, therefore, that grooves 24 must align with notches 16 in the base annulus when second annulus 3 is appropriately positioned and locked therein.

As shown in FIG. 7D, a substantially L-shaped locking channel 26 is formed in opposite sides of the external surface 23 of skirt 22. Each locking channel 26 has two sections, a substantially rectangular section 26A and a substantially square section 26B. As seen in FIG. 7C, section 26A has a uniform depth. However, section 26B has a bottom ramp 28.

That is, the depth of section 26B decreases from the juncture with section 26A to the juncture with the outer surface 23 of skirt 22. Thus, ramp 28 angles up from section 26A to surface 23.

Figure 3:
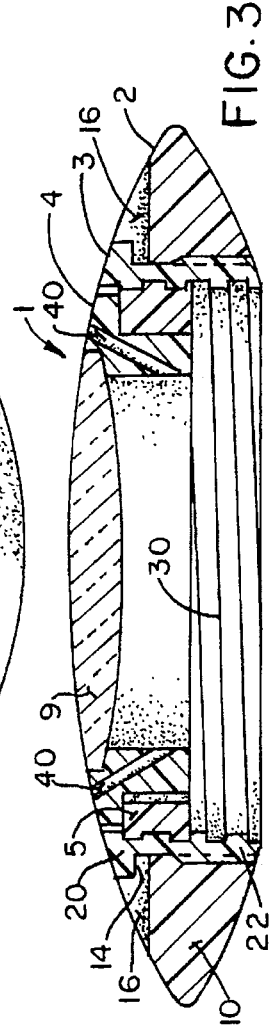
FIG. 3 is a cross-sectional view thereof taken along line 3—3 of FIG. 2.
Figure 8A:
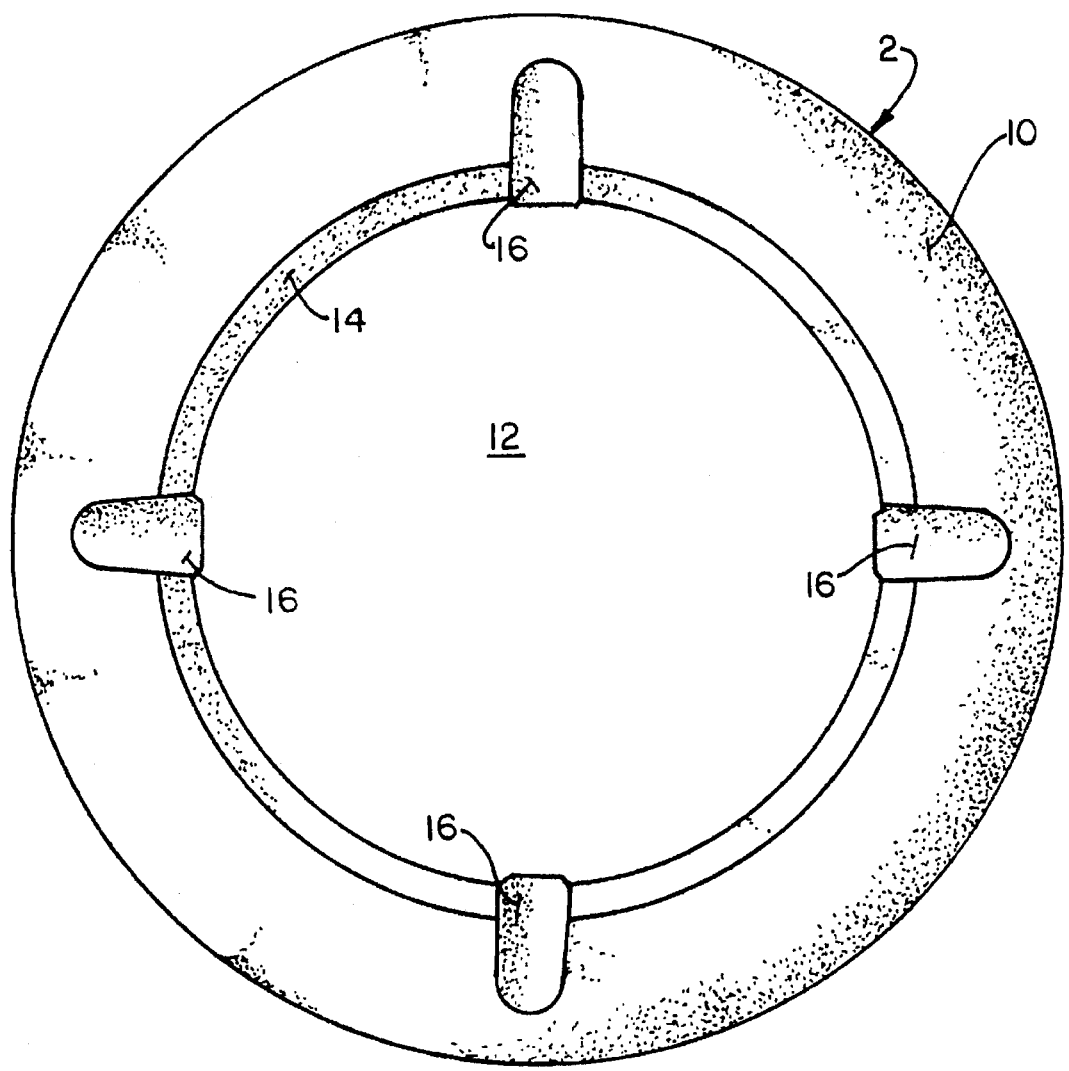
FIG. 8A is a front plan of the base annulus of the adjustable ocular implant of the present invention.
Figure 8B:
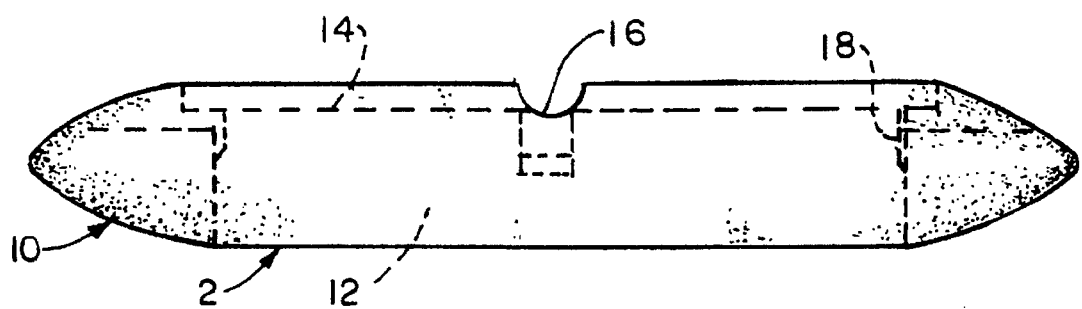
FIG. 8B is a side elevational view thereof.

As should be appreciated, the L-shaped locking groove 26 is intended to align with the detents 18 of annulus 2. When skirt 22 of second annulus 3 is inserted into opening 12, the detents 18 engage section 26A of locking groove 26. Annulus 3 is urged into the base annulus until outer ring 20 is seated in rabbet 14. Once properly seated, an appropriate tool is inserted through notches 16 to engage V-shaped grooves 24 on the outer ring of the second annulus. Annulus 3 is rotated so that the detents 18 slide up ramps 28 of groove section 26B. Annulus 3 thus is held in place by the bayonet-like lock. Moreover, there is a snug friction fit between the respective detents 18 and the ramps 28. The second annulus can be removed from the base annulus and lifted out of the eye so that the rotatable lens assembly can be changed with less stress on the base annulus and on the rotatable lens assembly. As seen in FIGS. 3 and 7B, the inside of skirt 22 has threads 30. Threads 30 are designed to threadedly engage a lens mount assembly.

In one preferred embodiment, as stated above, the lens mount assembly consists of a lens mount 4, shown in FIGS. 5A and 5B and threaded ring 5, shown in FIGS. 6A and 6B. As best seen in FIG. 5A, lens mount 4 has an outer ring 32 with beveled face 33 and a concentric annular skirt 34. Ring 32 has a rabbet 36 dimensioned to seat a bi-convex lens 9 (FIGS. 4A and 4B) or other appropriate refractive lens. Lens mount 4 can hold a filter or other element, as will be discussed below. Also, an overlying soft pliable toric lens of silicone, Teflon or other biocompatible material can be placed over the top of lens 9 if required, rather than in the lens chamber with separate slip friction ring for spherical power or astigmatic correction. Skirt 34 has an alignment spine 38 on the outer surface. A plurality of fluid flow channels 40 extend from face 33 through ring 32 and through the skirt. The fluid channels 40 are formed at an angle of approximately 60° relative to the axis of the lens mount and function to allow the ingress and egress of ocular fluids and maintain and even fluid pressure on both sides of the insert. In another embodiment, the fluid channels could be filled or impregnated with pharmaceutical agents such as antiinflammatory drugs, antibiotics or glaucoma agents for treatment of particular diseases. Alternatively, small pockets (not shown) filled with drugs could be included in the lens holder (or the base annulus or second annulus). The pockets could be opened with laser energy to allow the slow release of the medication.

The lens mount 4 is designed to seat in threaded ring 5, as shown in FIG. 6B. Ring 5 has a smooth interior surface and external threads 42. Threads 42 are disposed to engage the internal threads 30 of skirt 22 of second annulus 3 as will be explained below. Threaded right 5 defines and generally circular opening 44 dimensioned to seat skirt 34 of lens mount 4 with a snug friction fit. There is an alignment groove 46 formed in the internal face of the ring. During assembly, alignment spine 38 of lens mount 4 is positioned in groove 46 to ensure appropriate positioning. Once lens mount 4 is snugly secured in ring 5, ring 5 can be threadedly engaged in the second annulus. As will be appreciated, the entire lens mount assembly can be rotated within the second annulus to focus lens 9. The multiple piece lens mount assembly just described affords added flexibility in that ring 5 can remain threadedly engaged in annulus 3 when lens mount 4 is extracted from its snug friction fit within ring 5 to change lens 9, for example. This arrangement allows for less trauma to other components of the insert and to the patient.

Alternatively, adjustable ocular insert 1' illustrated in FIGS. 9A and 9B employs a lens mount of a unitary construction, indicated by reference numeral 7. Lens mount 7, best seen in FIGS. 10A and 10B, has an outer ring 50 having a beveled face 51 defining a rabbet 52 to seat a lens 9 or the like. Lens mount 7 also has a plurality of fluid paths 54 of the design previously described. Lens mount 7, however, has an integral, externally threaded skirt 56 with threads 58 designed to engage the internal threads of second annulus 3. Lens mount 7 is simpler and employs one piece. However, it does not afford the flexibility of the previously described lens mount assembly. That is, the entire lens mount 7 must be unscrewed from annulus 3 in the event lens 9 must be changed.

Regardless of the design of the lens mount, the lens mount can be rotated within annulus 2 to change the focus of the lens. The lens mount is rotated to move the lens forward or backward so to adjust and fine tune the refractive power and focusing for hyperopia, myopia and astigmatism. The intraocular implant has a power range of approximately 1 to 3 diopters. For example, predetermined movement of the lens mount could result in a predetermined change in power. For example, rotation of the lens holder 1 mm could result in a change of 3 diopters; 0.5 mm of rotation inside the eye could have plus or minus 1.5 diopters of focal power in the back of the eye. Therefore, the device with have a correction range of 0 to +3 diopters and 0 to −3 diopters. Prism range is from 2 to 6 with the prism base up, down, in or out. The prism will be rotary and can be turned to any meridian, other than the four cardinal directions.

It should be noted that fixed marking could be made on the face of the lens holder 4 and the second annulus 3 or base annulus 2 so that alignment of the respective marks would result the setting of a predetermined dioptric power. That would make precise adjustment predictable.

Various changes and modifications may be made in the ocular implant of the present invention without departing from the scope of the appended claims. For example, FIG. 5C illustrates another lens holder, indicated generally as 4'. It will be noted that lens holder 4' has a substantially shorter skirt 34'. Another lens mount, indicated generally by reference numeral 4" in FIG. 5D has an intermediately sized skirt 34". By varying the length of the respective skirts 4', 4 and 4", the physician can vary the surface area of contact between the lens holder and ring 5. If it is anticipated that the lens will be changed frequently, lens holder 4' or 4" may be employed since they would be easier to withdraw from ring 5. On the other hand, lens holder 4, although still removable, is more difficult to extract than other embodiments.

Since the lens holder is removable, the ocular insert of the present invention allows for upgradability of ocular or lens material to allow for greater optical resolution and purity. Further, various lenses, prisms, filters such as U.V., polarizing, infrared, blue light or photochromic filters and/or lenses, and/or combinations or permutations could be carried by the lens holder. Moreover, base annulus 2 can serve as a mounting means for future innovation in optics such as electro-optical devices, photosensors, photo power packs and mechanical medical devices. Sighting or alignment devices also could be employed. For example, lighting lines and leveling lines can be adjusted for equilibrium, orientation, measurement and stability. Also, it will be appreciated that an overlay lens can be placed over the lens for astigmatic correction of +1 to +4.

In view of the various changes and modification just described, it will be appreciated that the foregoing description and accompanying drawings are intended to be illustrative only and should not be viewed in a limiting sense.

We claim:

1. An adjustable intraocular lens assembly comprising;

a base annulus;

a second annulus secured within said base annulus;

a lens holder threadedly engaged in said second annulus, said lens holder bearing a corrective intraocular lens wherein rotation of said lens holder within said second annulus changes the refractive power of said corrective intraocular lens.

2. The lens assembly of claim 1 wherein said second annulus is removably secured within said base annulus with a bayonet lock.

3. The lens assembly of claim 1 wherein said second annulus has internal threads and said lens holder has external threads and said lens holder can be rotated within said second annulus.

4. The lens assembly of claim 1 wherein said second annulus is removable from said base annulus so as to allow the replacement of said corrective intraocular lens.

5. A rotatable lens implant comprising:

an annular base mount;

an internally threaded annulus removably mounted within said base mount;

an externally threaded lens mount rotatably mounted within said threaded annulus; and an intraocular lens removably mounted in said lens mount.

\* \* \* \* \*